(12) United States Patent
Young (10) Patent No.: US 11,274,635 B2
(45) Date of Patent: Mar. 15, 2022

(54) PRECISION DEPTH SENSOR

(71) Applicant: Gregory E. Young, Prescott Valley, AZ (US)

(72) Inventor: Gregory E. Young, Prescott Valley, AZ (US)

(*) Notice: Subject to any disclaimer, the term of this patent is extended or adjusted under 35 U.S.C. 154(b) by 39 days.

(21) Appl. No.: 16/666,183

(22) Filed: Oct. 28, 2019

(65) Prior Publication Data

US 2020/0063693 A1 Feb. 27, 2020

Related U.S. Application Data

(63) Continuation-in-part of application No. PCT/US2018/030020, filed on Apr. 27, 2018.

(60) Provisional application No. 62/491,882, filed on Apr. 28, 2017.

(51) Int. Cl.
| | |
|---|---|
| *F02M 21/02* | (2006.01) |
| *G01N 27/06* | (2006.01) |
| *G01N 33/28* | (2006.01) |
| *G01N 27/22* | (2006.01) |

(52) U.S. Cl.
CPC ............. *F02M 21/02* (2013.01); *G01N 27/06* (2013.01); *G01N 33/2847* (2013.01); *G01N 27/223* (2013.01)

(58) Field of Classification Search
CPC ................................ F02M 21/02; G01F 23/14
USPC .................................. 73/292, 296, 300, 302
See application file for complete search history.

(56) References Cited

U.S. PATENT DOCUMENTS

| | | | | |
|---|---|---|---|---|
| 3,038,336 | A * | 6/1962 | Peters | G01F 23/18 73/299 |
| 3,638,490 | A * | 2/1972 | Buettner | G01F 1/00 73/861.65 |
| 3,640,134 | A * | 2/1972 | Hop | G01F 23/14 73/299 |
| 4,807,201 | A * | 2/1989 | Fryda | E21B 47/06 367/908 |
| 4,852,054 | A | 7/1989 | Mastandrea | |
| 4,885,931 | A * | 12/1989 | Horner | G01F 23/14 73/49.2 |
| 5,189,904 | A * | 3/1993 | Maresca, Jr | G01M 3/2892 73/40.5 R |
| 5,263,371 | A * | 11/1993 | Maresca, Jr | G01F 23/2962 181/124 |
| 5,415,033 | A * | 5/1995 | Maresca, Jr | G01M 3/2807 73/40.5 R |
| 5,791,187 | A * | 8/1998 | Chang | G01C 13/008 73/290 R |
| 5,883,815 | A | 3/1999 | Drakulich et al. | |

(Continued)

FOREIGN PATENT DOCUMENTS

WO    WO 2008064010    5/2008

*Primary Examiner* — John Fitzgerald
(74) *Attorney, Agent, or Firm* — Bycer & Marion, PLC; Matthew L. Bycer; Michael B. Marion (57) ABSTRACT

A system and method for monitoring liquid tanks that includes a submersible sensor within the tank below liquid surface. The system may also include a secondary sensor to determine ambient conditions, and a controller to determine when changes in liquid level are due to ambient events, or potential breach of system. A calibration rod may be used to monitor displacement of liquid in the tank and calibrate system to determine changes in height of liquid level.

14 Claims, 4 Drawing Sheets

(56) References Cited

U.S. PATENT DOCUMENTS

| | | | | |
|---|---|---|---|---|
| 6,125,697 | A | * | 10/2000 | Holton ................ G01F 23/0038 324/207.14 |
| 6,351,993 | B1 | * | 3/2002 | Schellenberg ........ G01F 23/162 73/290 R |
| 6,606,905 | B2 | * | 8/2003 | Carroll .................... G01F 23/14 73/299 |
| 6,911,830 | B2 | * | 6/2005 | Heremans .............. G01N 27/06 324/698 |
| 7,143,634 | B1 | * | 12/2006 | Major ................ G01M 3/3263 73/49.2 |
| 7,251,998 | B2 | * | 8/2007 | Gourlay .................. G01F 23/14 73/290 R |
| 7,470,060 | B1 | | 12/2008 | Hoben et al. |
| 7,543,925 | B2 | * | 6/2009 | Ishizawa .............. B41J 2/17513 347/85 |
| 8,268,629 | B2 | | 9/2012 | Coleman et al. |
| 2003/0033871 | A1 | * | 2/2003 | Carroll .................... G01G 3/12 73/299 |
| 2004/0036487 | A1 | * | 2/2004 | Heremans .............. G01N 27/06 324/698 |
| 2006/0215002 | A1 | * | 9/2006 | Ishizawa .............. B41J 2/17556 347/86 |
| 2008/0150552 | A1 | * | 6/2008 | Straub .................... G01N 33/18 324/664 |
| 2014/0260601 | A1 | * | 9/2014 | Demin .................... G01F 23/72 73/305 |
| 2015/0120477 | A1 | | 4/2015 | Stevenson et al. |

* cited by examiner

PRIOR ART

PRECISION DEPTH SENSOR

CLAIM OF PRIORITY

The present application includes subject matter disclosed in and claims priority to PCT application entitled "Precision Depth Sensor" filed Apr. 27, 2018 and assigned Serial No. PCT/US18/030020, and provisional application entitled "Precision Depth Sensor" filed Apr. 28, 2017 and assigned Ser. No. 62/491,882, herein incorporated by reference describing an invention made by the present inventor.

BACKGROUND OF THE INVENTION

1. Field of the Invention

The present invention is directed to petroleum-based tank sensors, and more particularly related to storage tank monitoring and maintenance via testing for leaks in the system.

2. Description of Prior Art

In the retail petroleum industry, it is important to identify and recognize that underground and aboveground petroleum storage tanks, as well as other containers such as Under Dispenser Containment ("UDC") and sumps (to retain leaking fuel, keep water out, contain pumps, access to tank probes and sensors, etc.), are not leaking. These tanks, sumps, and UDC's (generally referred to as "tanks") are usually interconnected by pipe. This means that the tanks, UDCs, and sumps are penetrated (e.g. by the pipe) at various locations. These penetrations, along with above-identified used, and the unused, tank top penetrations (bungs), as well as the fuel vessel itself, need to be monitored and tested to ensure the tanks, sumps, UDC's, pipe and other penetrations, as well as the above describe fueling accessories, are not defective or leaking. Many of the systems of concern are on-site and see relatively minimal use (as compared to tanks at retail fueling stations).

Identifying Water/Phase Separation

Part of the United States Federal law concerning tank monitoring requires the detection of ingress of water. As water separates from the fuel (e.g. diesel), or water finds it way in with a fuel delivery, or water leaks into the tank, this water accumulates at the bottom of the tank. Floats specifically designed to track water at the bottom of fuel tanks are common. These floats can rise when the density of the fluid at the bottom of the container is greater than that of fuel. However, the use of ethanol in gasoline and biodiesel in diesel have changed the ability to detect the ingress of water. These two components, ethanol and biodiesel, both absorb water and mix (or dissolve) well with the respective fuel—thereby modifying the density of the separated liquid(s). The accumulation of water in these fuels has adverse effects on both the fuel and the storage vessels. The ingress of water is difficult to detect if it is being absorbed into the fuel.

The accumulation of water in ethanol blends can reach a saturation level, or maximum dissolved amount for a specific temperature and ethanol content of the fuel. If the fuel temperature falls due to a load of cool fuel, or temperature equalization with the environment, or other event, the ethanol/water (as a mixture that was previously in suspension) can fall to the bottom of the tank. This is known as phase-separated fuel. Immediately upon phase separation, the octane level changes (falls) in the remaining fuel due to the loss of ethanol in the fuel. This modified fuel can impair/degrade potential engine performance, damaging the engine, and possibly ruining the engine. The phase-separated fuel is more aggressive to the inside of the tanks; steel, coated steel, or fiberglass. This phase-separated fuel is also a feeding/breeding ground for biological and fungal activity within the tank or elsewhere. The biologicals, particularly the acetobacter bacteria, propagate in this environment. The acetobacter excretion includes acetic acid. This acid, and chemical stew, creates what was predicted and called a "cauldron effect". The cauldron effect is a potentially aggressive mixture that attacks bare steel, softens the gel/fiberglass coating of steel tanks and of fiberglass lined steel tanks, and is known to expose the mesh, weakening the structural integrity of a fiberglass tank such that containment has failed on tanks, steel and fiberglass.

The phase-separated fuel can build up on the bottom of the tank until phase-separated fuel is close enough to the pump inlet to enter the fuel distribution system and be dispensed into vehicles.

Fuel in the fuel storage tank that is not phase-separated, but is high in dissolved water content, can be pumped into an automotive tank. The vehicles drive off, and some of the vehicles may be stored indoors. Whether due to storing in cool areas (e.g. A/C garage) or due to storage in outside areas that the temperature cools diurnally, the temperature of the fuel tank falls to a point to cause phase-separation inside the automotive fuel tank. Phase-separated fuel begins degrading the fuel tank and components in the fuel system.

Water also affects diesel fuels. The accumulation of water in the bottom of a tank provides a fuel water interface that allows microbes to rapidly propagate. This interface can grow significant biomass plugging filters, a particular type of bacteria (acetobacter) can acidify fuel causing tank and equipment degradation.

Most diesel fuel today is mixed with biodiesel to meet Federal fuel guidelines. The Sulphur content is reduced in fuel today. Biodiesel adds lubricity to the fuel, a desired addition due to the reduction of sulfur that used to provide a higher level of lubricity to diesel. Biodiesel absorbs water. Bacteria and molds grow in the biodiesel fuel in part due to the water in the fuel. The fuel is acidified by the acetic acid waste of the acetobacter bacteria growing in the fuel. Bacteria and debris fall to the bottom of the tank. During a fuel delivery the debris and bacteria are pushed around the tank, up to and including the edges of the tank. As the particles are pushed together, chemists recognize these groups as colonies. The colonies "slime" themselves, protecting the colony. This protection increases the survivability of the colony, protecting them from chemical means of killing bacteria in the tank. These colonies excrete acid, concentrating the acid next to the tank in a way that it is not easily dispersed, damaging/destroying steel, softening/damaging the gel coat and fiberglass. Tanks fail in many ways, and may compromise containment of liquid (such as fuel, etc.) stored therein.

Prior art solutions include magnetostrictive level probes for sensing changes in fuel level within tanks. Magnetostrictive sensors provide high resolution level sensors via a magnetostrictive stem float, or probe level sensor. This continuous liquid level solution is able to determine level within only a few millimeters. Magnetostrictive sensors work by using a ferromagnetic metal, which aligns itself with magnetic fields. By creating two competing magnetic fields, the magnetostrictive level sensor is able to generate a signal denoting the liquid level.

A magnetostrictive probe is built by suspending a ferromagnetic metal wire inside a long stem. Electronics at the top of the stem generate an electrical pulse that travels down the wire, at regular intervals. This creates the first magnetic field. The second is created by a magnet inside a float that moves up and down the stem with the liquid level. When the electrical pulse reaches the float, and the two magnetic fields collide, the metal wire inside the stem twists, and a vibration is sent back up the wire to signal change in fuel level.

There currently exists a need for more careful monitoring, adaptive dynamic monitoring, and monitoring systems that avoid corrosion and other means of adding impurities to the fuel line. Therefore, it is advantageous to have a small, robust, portable test method that can perform precision tests to detect leaks. Tanks, sumps and UDC's (Under Dispenser Containment) are designed to prevent fuel from polluting the surrounding area. If the fuel leaves these containments, the ground will become polluted, potentially polluting groundwater, potentially polluting indoor vapor-space by migrating through soils and entering buildings, subways etc.

There is a need in several industries, but notably, the petroleum and the chemical industry to provide a leak detection method that provides the ability to integrate several test methods that can report information in several formats, having the ability to test multiple fluids in liquid form.

Therefore a PDS (Precision Depth Sensor) can provide a compact, robust measurement device, part of a method to be sure sumps and UDC's and the penetrations through them are not allowing moisture/water to penetrate into or fuel out of the containment devices.

It is therefore a primary object of the present invention to provide monitoring of fuel conditions within a tank.

It is another object of the present invention to provide a system to monitor fuel conditions within a tank.

These and other objects of the present invention will be made clear in light of the further discussion below.

SUMMARY OF THE INVENTION

The present invention is directed to a method of determining the qualities of a liquid in a storage tank with an embedded sensor submerged into the liquid. Preferably, the embedded sensor is set along a bottom surface of the storage tank, or not more than a two or a few inches above the bottom surface of tank, preferably about one-half to one-inch or less suspended above bottom of tank, preferably near lowest portion of tank bottom. A displacement rod may be used to calibrate the measurement via use of a submersion. Conditions may be determined of the tank of fluid via coordinated submerged sensor within the fuel, and a secondary sensor to determine ambient conditions. An initial pressure may be measured along a specific point in the bottom of the tank. The weight of the fuel can then be determined based on an initial pressure reading, often along with a measurement of fuel volume. Then one may calibrate the measurement via use of a submersible displacement rod via suspending a (preferably vertical cylindrical) rod of a set volume into the fuel. When the rod is emplaced within the fuel at a specific height and/or volume, one may detect a new further pressure from the PDS embedded sensor. Thereby, one may determine a change in the pressure as between the initial pressure and the further pressure readings. By using a pressure differential to determine a pressure to volume ratio, one may thereafter monitor the pressure reading at the sensor. Concurrent ambient conditions may be monitored simultaneously and in conjunction with readings in embedded sensor, such readings to be correlated to determine if ambient conditions change cause changes in embedded sensor readings (e.g. as by expansion of fuel due to temperature). Concurrent ambient readings may be made within tank (near top (in ullage)), and/or at or near exposed surface above-ground, and/or shallowly buried within ground surface, and/or along exterior surface of tank below ground.

A TCV formula may be used to determine if differences of fluid level over time are due to natural ambient conditions, or system failure. The conditions within the fuel are determined by a sunken probe. The probe may rest on the bottom of a fuel storage tank, and/or the probe may rest just above (within an inch or inches) of the bottom of a fuel storage tank. A probe may determine the conductivity or resistance of the liquid, and may compare resistance with the expected change of system conditions reported by a simultaneous system or outside system sensor. A probe may determine the properties of a stored liquid, and compare those properties with the expected change of system conditions reported by a simultaneous system or outside system sensor.

The present invention also includes a system for monitoring the fuel level in a tank, and determining when changes in the fuel are due to leakage. The system is a precision depth sensor that includes a submerged sensor below the fuel level within the tank, wherein the submerged sensor may include a pressure transducer and a power source, or offboard power source connected via wireless or wires. The system also includes a controller for determining or monitoring pressure sensed by the submerged sensor and compare to expected levels. A displacement rod may be used to calibrate the system by moving between a position at least partially outside liquid in tank, and a position at least more partially within fuel of tank. Preferably, a secondary sensor outside the liquid of the tank, either within tank (towards top, or outside tank may be used to determine ambient conditions and help coordinate determination of the expected fuel level.

BRIEF DESCRIPTION OF THE DRAWINGS

The present invention will be described with greater specificity and clarity with reference to the following drawings, wherein like numerals designate like parts, and in which.

DETAILED DESCRIPTION OF THE PREFERRED EMBODIMENTS

The nexus of the PDS was how to provide a means of measurement of liquid for different applications, one that did not have the same problems as prior art magnetostrictive probe. Prior art probes typically have a short lifespan, the cables grow bacteria or corrode, and the results lose accuracy while testing sumps. Tanks, particularly tall tanks, provided very low resolution due to tank size and mounting issues of the probes. The corrosion and particulate issue of the prior art is a problem for the magnetostrictive probe.

One application may include digitally provided a means of line testing, recording the information electronically in real time, without requiring a human to make readings by sight, entering the info and then calculating the results.

The PDS, as presently described. Provides a higher resolution, allows monitoring smaller liquid level movements, for regular tank testing and sump testing. Technology has now advanced with smaller, faster, portable computers and higher resolution ADC devices, to allow the PDS device to become a viable technology.

A housing protects the electronics as the PDS sensor is submersed. The PDS system provides a program to record appropriate information and transmit it to provide calculations.

Measuring Leaks

The primary method to determine the integrity of the portion of the tank holding liquid in retail fueling stations is via the use of probes. These probes are combined with a computer/controller/processor, a.k.a. monitoring system. The computer processes signal information from the probe to establish the liquid level height and fuel temperature inside the storage tank. This liquid level information is compared to tank charts (preferably stored in the computer) to establish the fuel volume in the storage tank. The temperature information is used to calculate the volume change of the fuel due to thermal expansion or contraction as calculated Temperature Compensated Volume or TCV:

Fuel volume×Temperature change×Coefficient of expansion=TCV

Leak rates are calculated by the results of TCV and time. The testing of the area of the tank that does not have liquid is tested in other methods not addressed here.

The calculated change of fuel volume (fuel volume plus or minus the fuel volume change from the change of temperature) is compared to the measured fuel volume (height). If the equipment is accurate, and the calculations are accurate, and the tank charts are accurate, the TCV should equal the tank volume. Therefore, TCV should accurately track and compensate for changes in liquid temperature and/or volume. Changes in volume can also be caused by leaks out of the tank, and/or due to the ingress of liquid (usually water). It is also possible to compromise systems when the tank is sitting in an area that retains liquid (such as clay), that effectively makes a containment area (soil or substrate) that water or fuel moves very slowly into and out of. This contained liquid can move in and out of leaking tanks and compromise purity of contained fuel.

Figure 3:
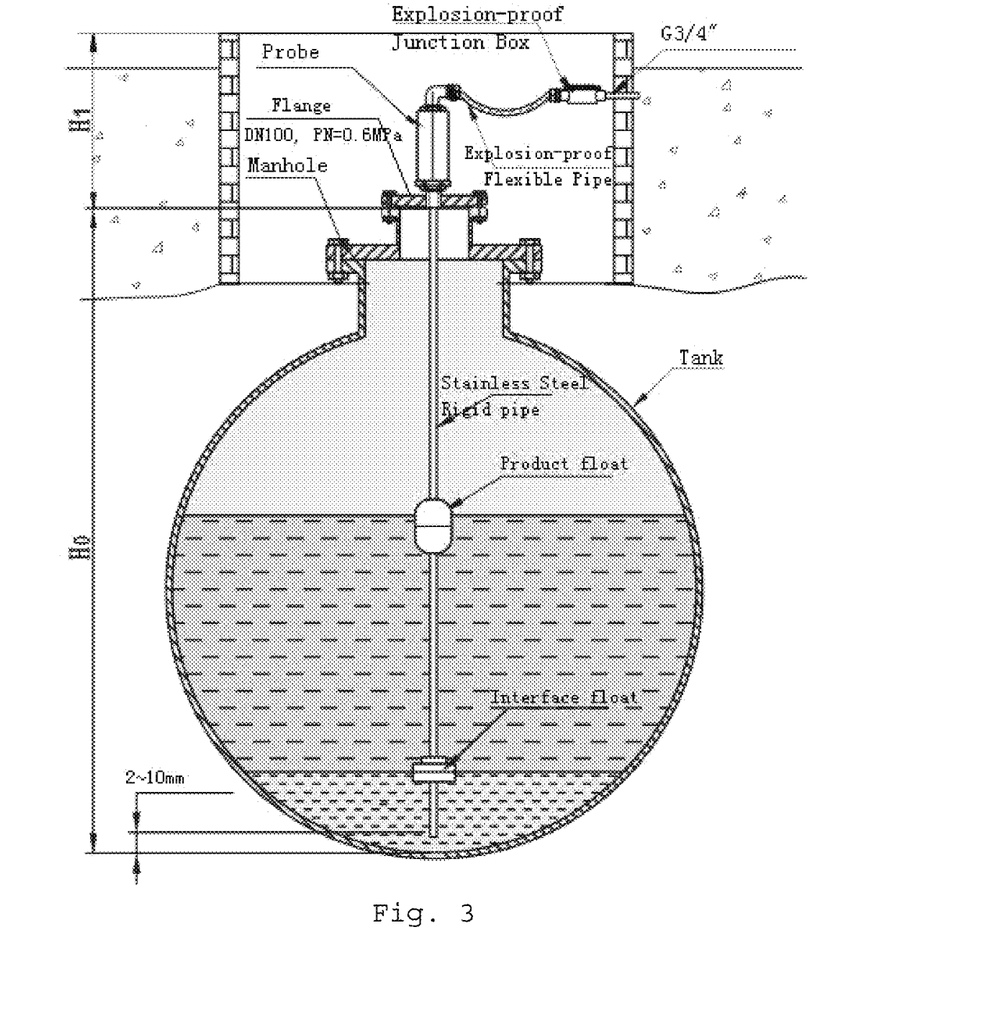
FIG. 3 demonstrates an underground storage tank of prior art with magnetostrictive sensor.

Prior art solutions include magnetostrictive probes, as seen in FIG. 3. A well-known issue with magnetostrictive probes is stickage. Stickage is the effect of friction between the stick portion and the float portion of the probe. This problem is exacerbated if the probe is not straight up-and-down (vertical). Stickage is a significant issue when sump testing is done with magnetostrictive probes as the setup requires strict attention to ensure the probes have the least amount of friction.

Another issue with tanks and magnetostrictive probes, is the higher incidence of significant bacterial growth, including bio-film. The bacterial growth (mostly the acetobacter, but others contribute to this problem) is increasing acidity (lowering pH) and thereby destroying equipment (including tank surfaces) and increasing friction. Biofilm contributes to stickage, fouling of the stick/float interface.

Another issue identified with the increasing acidity of fuel is the amount of particles in the fuel due to the corrosion occurring inside the tank system. The corrosion is continually "stirred" and lifted into the fuel every time the tank takes a delivery. These particles are contributing to the float sticking problems. The high acidity is eating up the containment of the float sensors, rendering them less accurate or not functional. To combat issues of acidity, the PDS uses 316 stainless steel (as is known in the art) for wetted portions of the sensor, such as the shell or cylinder and caps, and treatment for steel components immersed in low PH fuel allowing long life in low PH fuels.

Calibration

It is important to have a Pretest or Diagnostic mode for sump and other containment testing. Today, testing equipment has a Pass/Fail method of reporting leaks. This is due, in part, that there is no acceptable leak rate allowed if it is detected. Currently, manufacturers use the mandated test threshold (such as 0.05 mph for tanks) or ⅛" per hour (for sumps) as the reporting threshold. Basically, any leaks below the threshold do not have to be reported, therefore the equipment is not designed to report it (either because it lacks sensitivity, or is programmed as such). When a technician is testing a tank or sump and there is a fail, failure could be due to one or multiple failure points below the threshold of detection required. If there are multiple points of failure, there is no tool to help the technician as to where these levels or failure points are located. Such is the need for a Diagnostic test, a tool that allows technicians to test levels of containments to find out if it is leaking a proportional share of the total leak.

In order for such a tool to be useful for Pretest or Diagnostic Mode, the sensitivity must minimally meet the ability to detect a proportional amount of the potential leak points. The PDS and sump test software is sensitive enough to detect as small as 0.0000001". As current sumps/containments do not normally exceed 10 penetrations, the PDS is such an appropriate tool. A variation of the PDS can exceed even greater sensitivity as described below, such as to detect 0.00005 gph or 0.000005 gph, depending on the size of the sump/tank the PDS is testing in.

Such a tool must be sensitive enough to give accurate information to detect leaks smaller than the aggregate of the leak threshold. It is suggested that in order for such a tool to help identify small leaks that could in total affect aggregate test results, it should be able to identify small enough leaks such that if each penetration was leaking a proportional amount, the test equipment could identify each leak, allowing the successful repair of the containment. Each leak could be repaired, in turn, while a test is made after each fix, until no detectable leaks remain. The Precision Depth Sensor combined with the appropriate software is such a tool for the retail petroleum industry and the current US EPA test thresholds as the penetrations in sumps that could leak.

Calibration Feature Example

PDS is placed in a tube of a known depth, such as 2 ft. Fill the tube to the top, such that excess liquid runs down the side into a secondary container. The weight per distance (height) is then determined. With weight of a predetermined height, we can now know precise height/weight changes. This will allow us to measure depths on fluids not in a pre-defined list or of an unknown product.

Track the temperature change of the "unknown" fluid in the same container. Weight per degree can be calculated so temperature compensated volume testing and monitoring can be accomplished. Ideally this would occur in real time so the testing and the temperature change could be identified as the liquid level change is recorded.

Additionally, where the fuel is in a container that allows changes in volume and growth due to thermal expansion or thermal contraction to be tracked, The COE (coefficient of expansion) could be calculated in the field, parallel to the testing that is ongoing. The addition of a calibration rod to this container is an additional method to check the sensitivity and accuracy of the information.

Due to equipment, pipes, plumbing, sensors, pumps, leak detection equipment, etc. the surface area of a sump is not the same as the surface area calculated of (empty) rectangles, squares, or circles, the typical shapes of sumps. Therefore, a method that allows an operator to calibrate the surface area allows the operator to report leak rate as the depth changes and the surface area allow the test system to report volumetric leak rate changes.

PDS embedded sensor should be ai a fixed position in tank. Sensor may be located in a fuel pipe (drop tube). The drop tube being sealed at a top may only be affected by ambient conditions. Ullage pressure and ambient pressure should be isolated (and may differ), allowing for more accurate readings.

The sensor should be set in a fixed position (as in other embodiments) and cannot be loosely suspended to allow random movement of sensor that may affect readings (unless location known). If material of sensor will move, or change size (as in a metal that expands/contracts with temperature, etc., such information is to be calibrated. The present system may include a pressure temperature monitor over a predetermined time. Static temperature within tank may be required to run tests. One may make multiple readings over time to detect a leak. Once may compare varied readings to determine a leak and leak rate. For instance, consecutive readings may not be compared, but a staggered comparison may be needed (e.g. comparing first and third reading with second and fourth, third and fifth, etc.).

Figure 1:
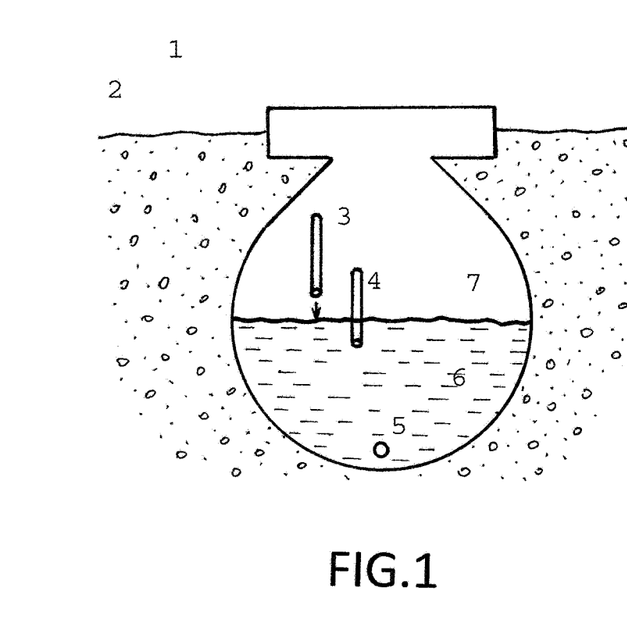
FIG. 1 demonstrates an underground storage tank with PDS and calibration rod in alternate positions.

For example, if after the setup of the equipment, including the deployment of a PDS in the bottom of a tank, a calibration mode in the attached computer was entered, a solid displacement rod of a known length/volume could be lowered into the tank liquid, as can be seen in FIG. 1. The calibration reading finishes. The rod is removed. This displacement of a known rod volume allows the surface area to be calculated based upon the detected height level (weight) change. Tank 1 is placed within substrate or soil or ground 2. Tank 1 includes fuel 6 with a top level 7. Sensor (PDS) 5 capsule, is preferably a cylinder, or capsule, or other structure. Rod 3 may be started at position 3 above level 7, and then lowered into fuel 6 at rod position 4. Both rods are shown for illustrative purposes of the position of a single rod. The volume of rod immersed is determined by the amount of fuel displaced and height of fuel, or vice versa. Sensor 5 may record weight, pressure, or the like. Sensor 5 may also determine temperate, electrical characteristics, etc.

The lowering of the displacement rod into the product at beginning of the test for calibration, then removing it, and repeating the test at the end by lowering the calibration rod into the liquid for a second calibration and removing it a second time would provide a second data point for calibration sensitivity that can be used to confirm the sensitivity, check if the values match, and if not within a statistical valid range, indicate the surface area has changed or some other variable has changed thus requiring compensation of other variables or a retest.

The lowering of the displacement rod in the beginning of the test to get a calibration and leaving it in the liquid during the test, removing the calibration rod at the end of the test also provides two data points to calculate surface area/volumetric changes and provides a check to insure the quality of the data from start to finish.

The parameters of the vessel such as shape and size affect the rate of change. For example, in liquid level change detection, if a vessel were larger on the bottom but the sides sloped inward towards the top of the vessel, the rate of change would slow down as the liquid left the vessel. The liquid level change per time interval would be less for the same volume of fluid that leaves a vessel with the described sloping walls verses a vessel that the sides did not slope. A means of determining this change and compensating for this type of variable would be beneficial to reporting accurate rate results.

Similarly, the above-mentioned sloping walls change the accuracy of volumetric reporting unless there is a method of determining how the surface area of the tank is changing and integrating that into the volumetric calculations or liquid level rate reporting.

Entering a slope calculation mode would allow the use of a displacement rod entered 3 times, once to establish a starting surface area, the second would establish a slope, percent change of a consistent slope, the third would either represent the continuation of the same slope, or a different value would represent either a leak, an ingress, or a change of the slope. The time between Calibration 1 and 2 and 2 and 3 must be varied by at least two times to differential slope and leak and slope results.

Not all exercises test the same material. For example, one system may have water as the test media, in another tank, diesel, yet another premium gasoline. Additionally, there may be a different exercise that tests for both water and hydrocarbon, but only in the liquid phase and not as suspended particles as in determining the volume or percentage of water suspended in a hydrocarbon such as diesel fuel.

Calibrating an Unknown Liquid

A user can enter a precise measurement of the current liquid depth. Using this information, we can back calculate the weight per fluid unit at one temperature. A calibrated fluid can be used for precision testing at one temperature. Without a coefficient of expansion (COE) we can only approximate actual fluid depths during temperature change. With several repeats of the current liquid depth as above and a new/changing temperature it is possible to closely approximate the COE for the temperature.

Dual Sensors

Figure 2:
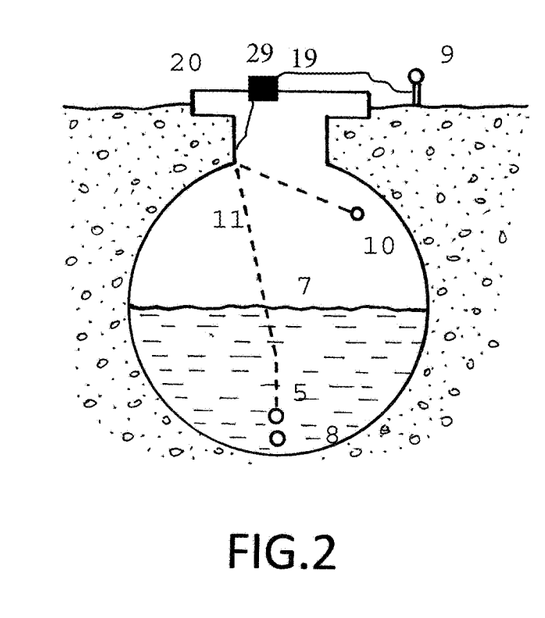
FIG. 2 demonstrates an underground storage tank with PDS and secondary sensor in alternate positions.

To ensure that the testing system is calibrated correctly, dual sensors may be employed. As can be seen in FIG. 2, Tank 1 includes contact with surface 20, such as through bung hole. First PDS sensor position 5 may be at a location just above the bottom of tank 1. Alternative position 8 for sensor, may be along bottom of tank. A wire 11 may be used to power PDS or otherwise transmit analog or digital signals to outside box (not shown). A second sensor location 10 may be used to determine ambient conditions, such as temperature, humidity, etc. A further alternative location 9 for secondary sensor may also be used on surface, or outside tank system. Both secondary sensors 9 and 10 may be used, or each may be used in isolation to support PDS submerged sensor 5. Further alternative location 9 may include an interface box, as described below. Connector wire 19 may pass through bung cap 29 to electronically and communicatively connect with embedded sensor.

For instance, weight, height, and/or volume, etc. of the liquid in the tanks is monitored. At the same time, a separate monitor of ambient conditions may be used to monitor the conditions of the greater system (i.e. atmosphere and geographic location). For instance, if as the test is running (or the system is being monitored) the ambient atmospheric pressure may change (i.e. barometric pressure, temperature, dew point, humidity, etc.) thus resulting in a change to the properties of the liquid that may impact one or more of the monitored variables. By correlating the instantaneous data from a sensor within the liquid to another sensor outside the liquid (for instance in the ullage of the tank, above ground, or elsewhere) changes in the fluid due to ambient conditions can be controlled. Therefore, changes that exceed expected response to ambient conditions may indicate a leak.

A first sensor may be placed to gauge atmospheric pressure above ground or in the ullage. A second sensor may be submerged within the liquid the tank (such as an underground storage tank, or above-ground storage tank). Both sensors may be connected in real-time to correct for sensor readings in the tank. Otherwise, the readings can be matched up at a later time, or in the analysis, to compare atmospheric pressure with readings in the tank to eliminate false triggers or masked leaks (false negatives and false positives).

Simultaneous data may be taken inside, and outside, the tank to test the weight of the fluid and ensure that it meets standards. Weight is determined by pressure on the submerged sensor. This data is compared with tables for standard compliance, with the additional data point of temperature.

Another embodiment of the present invention includes a test to determine quantity of water diluted in the fuel. This will help determine the risk—level that the water admixed in the fuel may separate given a major or minor change in conditions. For instance, if the water level mixed into the fuel is at the point whereby a drop of ten degrees to forty degrees in temperature will often cause phase separation (i.e. when dispensed into a vehicle fuel tank which may then be garaged or left out overnight), the system can indicate potential risk of future phase separation. Phase separation can occur wherein water drops from diesel, or ethanol/water mixtures drops or separates from ethanol modified gasoline. Current systems using a second, lower float (as can be seen in FIG. 3) may work between phase-separated diesel/water, but may not work in gasoline or gasoline/ethanol mixtures. Such a test may be conducted via determination of electrical resistance through the fuel, for instance via a probe with two separated terminals and running a voltage there between. Such an electrical sensor can also determine if the sensor is sitting in phase-separated fuel—based on the resistance between the terminals.

Use of electrical current to determine resistance, and thus properties of the fuel, may be conducted via a permanently affixed probe. This probe may determine the ongoing risk of phase separation (such as with expected or potential temperature drops, changes in conditions, or post-dispensation to vehicles. The probe, or any electrical resistance measuring system, can determine the amount of water in the fuel. The novelty of the present invention is the use of such a probe in a working tank, including tanks and an underground storage tank at, for instance, a retail fuel dispensary (gas station).

PDS provides for a more accurate reporting of fluid depth in tall/high tanks via use of multiple sensors. Finding level/leaks in large above ground storage tanks is difficult, the resolution is much greater if you are measuring tanks 15 ft. and under. One of the issues is the scale or sensitivity of the measurement devices. The same graduations are available in the devices used whether you are measuring 15 ft. or 125 ft. While time may allow a means of looking for change, it is impossible to achieve the same resolution with the magnetostrictive or pressure sensitive instruments currently used if you are having to expand the same scale you used for resolution over 15 ft. and apply it to 125 ft. Because Depth/pressure sensors/pressure transducers (magnetostrictive probes also) have a resolution scale, the distance or weight that sensors are used for (pressure or distance range that is to be parsed) sets the precision that can be obtained. If multiple depth or magnetostrictive sensors are used, say mounted on a rod or to precision distances from each other, the precision of smaller set depth/weight ranges could allow significantly higher precision results, allowing almost any desirable precision by the placement/scale chosen. Allowing a pressure overlap, a controller could decide which sensor was read/reported. The overlap would be to allow each sensor to work within its range and the desirable sensitivity such that one is no longer read/reported as the pressure range leaves the assigned parameters of the defined area of the sensor above or below the specific pressure the intended sensor is depended upon for accurate information.

PDS allows a system to be Diagnosed, not only Tested. Diagnostic is different from Testing from a regulatory perspective in that a Fail is an actionable item from a regulatory perspective. A Diagnostic mode allows sumps and other containers to be checked before a regulatory Test must be performed. An example would be the need to repair a fitting or connector that has obviously failed, then check the sump to see if your repair is "holding" or working as desired. The repair may not be the top fitting, so the sump may be tested at the level of the penetration, this is not Testing all the penetrations. Additionally, a Diagnostic may be run after a sump has failed. Detecting at what level the leak is located might entail testing from the top down or bottom up, each penetration, the effects of height (pressure) determining the use of each or both methods of testing.

Figure 4:
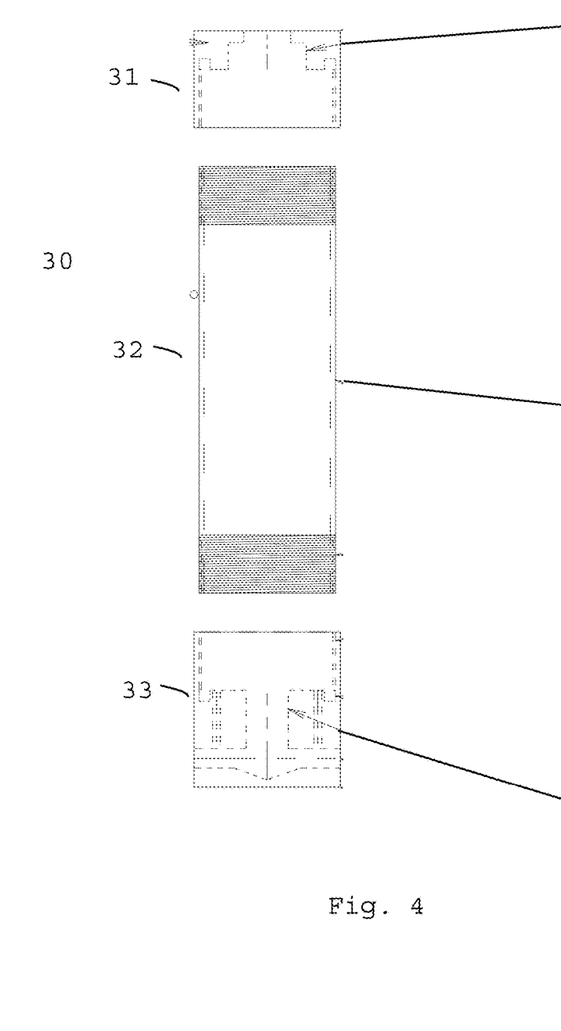
FIG. 4 demonstrates exploded view of PDS sensor.
Figure 4A:
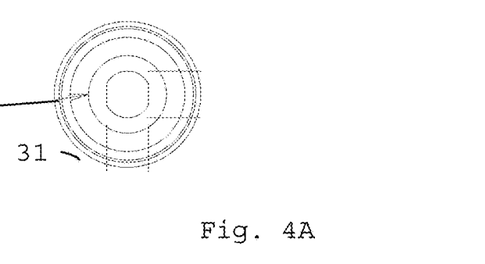
FIG. 4A demonstrates a cross-section of top of PDS sensor.
Figure 4B:
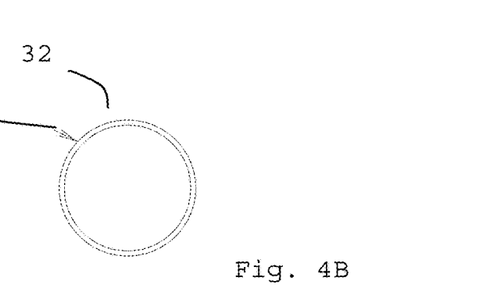
FIG. 4B demonstrates a cross-section of center of PDS sensor.
Figure 4C:
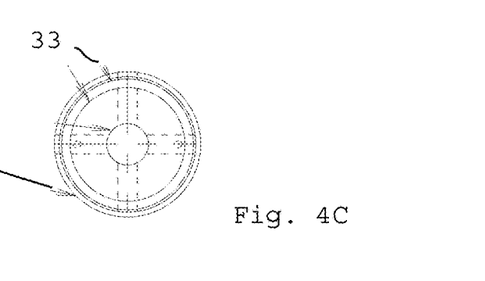
FIG. 4C demonstrates a cross-section of bottom of PDS sensor.

It is well known that determining the height of a fluid can be obtained by measuring the weight of a fluid (from a point such as the bottom of a vessel) given certain known parameters such as: the fluid weight (density) at a specific temperature; temperature of the fluid; pressure on the fluid—Such as barometric pressure, etc. To determine change of fluid height it is important to: know elapsed time from one reading to the next (or the time of a Beginning/Ending Test cycle); know the temperature of the fluid at the measurement intervals; know the pressure on the fluid when the measurements are made (barometric or other); and compensate for changing temperature and pressure on the fluid during measurements The PDS is a digital submersible pressure sensor, as can be seen in FIG. 2. As can be seen in FIG. 4, the electronics and sensors should be in enclosures that are water tight, except for the opening of the sensor measuring pressure. The enclosures are preferably round. The enclosure is preferably lowered to the bottom of a tank or containment sump using its data cable. The sensor is preferably powered by very low voltage. A battery may be used to allow the PDS sensor to remain submerged without wiring required. The PDS sensor could communicate via wireless to a receiver either at top of tank (either along a second internal tank sensor, or near the bung), or outside of tank system. Alternatively, the PDS submerged sensor can be connected to the tank, and may receive power via current in an electrically conduction along a metal tank surface. Alternatively, the PDS sensor may be mounted onto a specialized tank surface near bottom of tank, either along surface of tank or a few inches above the surface and receive power there through. PDS sensor may sit at bottom of tank, or alternatively be suspended floating at a known height within fuel. A thin wire may be used to provide power to PDS sensor from outside tank system to provide power from a small battery, and/or solar cell power source.

The PDS sensor enclosure (or PDS) is used to encapsulate the buried sensors (within the fuel). The enclosure may include an opening to allow the fuel weight to be on the transducer. The transducer is soldered to the board within the sensor. The ADC (Analog Digital Converter) is marked on the board. Preferably the ADC is in very close proximity to the pressure sensor connect. Preferably, the pressure sensor connects to the ADC, the ADC through to the processor. The processor board may sit above the PCB, the connections through the black ovals to the left and right of the oblong area marked that the ADC and RS-485 is in.

While this is the current configuration, alternative configurations may include circular boards that stack on top of each other in several layers within sensor. In such an arrangement, the pressure transducer in communication with the liquid in the sump or vessel can be on one end. The transducer connected to the ADC, to the processor and terminating with a liquid proof seal that allows RS 485 communication to the interface box. The interface box contains a means for the pressure sensor to read ambient air pressure and communicate back to the processor in the liquid, allowing compensation for weight of the air pressure pushing down on the liquid we are testing. The interface box may also allow multiple PDS's within the same tank, or networked tanks, or multiple unrelated tanks, to communicate to the computer through a USB connection. The interface box may be a USB hub for the sensors and a means to provide pressure to the individual PDS sensors. It also provides the "key" for the sensors to communicate with our program.

The "Board or boards" are located in the PDS, mounted longitudinally in the circular PDS. The PDS sensor may be connected by tube/wire to a point at top/inside tank, or outside of tank through bung. In sump deployments, the top may be open, so the connection would be straight through to the interface box, to the computer. Used to monitor a tank, the connector from the PDS would pass through a bung that has a cap that allows the wire to pass without allowing vapor out or liquid in to the tank. Such sealing could be through already existing compression fittings, or through a plug that is mounted in the cap with vapor barriers, that allow connections to be made on both sides of the cap, passing the appropriate information through said connector.

The PDS sensor, using pressure and temperature measurement, can allow determination of a temperature compensated level and/or TCV. Temperature may be measured from a sensor embedded in the housing liquid path(s), and/or elsewhere within tank, and/or outside of tank system. Free water 1" in depth can be detected with an intrinsically safe water detection circuit. Entrained water in fuel can be detected with an intrinsically safe water detection circuit.

All data conversions, filtering, and timed testing are performed in the PDS, an advantage as the potential of passing data that is corrupted by transmission errors or missed communications at the receiving equipment is reduced. The PDS communicates to a computer or controller over an intrinsically safe cable or through intrinsically safe wireless communications. Level may be reported to at least 0.0005 resolution. Temperature sensitive to 0.01-degree F. The sensor should be able to pass through a 2" NPT threaded opening for temporary deployments. The unit may be able to be calibrated to unknown liquid types.

Currently, no permanently installed or temporarily installed liquid level sensor used in the petroleum industry can also report entrained water levels (above ASTM standards for the liquid such as ASTM D6304-07, reporting 500 ppm or more water in diesel fuel or ASTM D6304-07 for gasoline, reporting 1,500 ppm water in gasoline). The addition of finding and reporting free water levels as low as 1" with entrained water, with a petroleum or other liquid level depth sensor is also not currently available in the prior art.

The present invention also includes the optional use of electrical conductivity, ohms or resistance, to determine the amount of water in fuel. While this is a test performed in labs, no one has combined it with a liquid level monitor to monitor fuel level/volume and suspended water, and free water, especially via two integrated methods of monitoring.

To determine the size or capacity of the tank, in tank gauging, or in tank testing systems, different tank configurations are resident such that an operator can enter length and width and height measurements of common dimension tanks of various configurations including square, oblong and round tanks that are horizontal or vertical. The tables for round, square, horizontal and vertical tanks show inches/volumes to account for changes of volumes as the diameter of the tank changes. There are charts that account for differences of the ends of tanks as fiberglass and steel tanks have different volume changes as the ends of the tanks are different. For instance, steel tanks have mostly flat ends and fiberglass tanks have a significantly larger bell on the end.

Similarly, dimensions of a sump can be manually entered to calculate surface area of a sump. Such methods are acceptable and commonly used. However, there are more automated ways that are more accurate and allow sumps that have difficult shapes or protrusions to determine surface area.

If the vessel has pipes or equipment inside the area to be tested, and the equipment or pipes are exposed. The volume of the liquid in the sump is not easily calculated.

The present invention includes a test method with:
a. The ability to test a wide variety of vessels: vertical, horizontal, round, oval, sumps, drums, transport tanks, etc. to determine if there are leaks. The shape, dimensions and protrusions of and in the tank affect accurate volumetric reporting. Due to equipment, pipes, plumbing, sensors, pumps, leak detection equipment, etc. the surface area of a sump may not be the same as the surface area calculated of (empty) rectangles, squares, or circles, the typical shapes of sumps. Protrusions in tanks Therefore a method that adds or subtracts known volumes can be used to "calibrate" a specific volume displacement to change in height to determine the volume change in tanks that have irregular shapes or protrusions such as pipes, pumps or other irregular shapes in the tank at the height of the tank;
b. in a vessel, determining the height of a leak from the bottom of the vessel.
c. Testing can be such that level change in a given time is the desired metric to evaluate an action point or a classification such as Pass-Fail It is well known that determining the height of a fluid can be obtained by measuring the weight of a fluid from a point such as the bottom of a vessel given certain known parameters such as:

The fluid weight (density) at a specific temperature
The temperature of the fluid
The pressure on the fluid—such as barometric pressure To determine change of fluid height it is important to: know elapsed time; know the change of the temperature of the fluid during additional measurements; know the change of pressure when subsequent measurements are made; and compensate for changing temperature and pressure on the fluid during measurements.

Testing can also be such that a volumetric amount is the desired result such as 0.1 gallon per hour. In order to report in volumetric measures, the parameters of the vessel are important. The shape, dimensions and protrusions of and in the tank affect accurate volumetric reporting. Due to equipment, pipes, plumbing, sensors, pumps, leak detection equipment, etc. the surface area of a sump may not be the same as the surface area calculated of (empty) rectangles, squares, or circles, the typical shapes of sumps. Protrusions in tanks Therefore a method that adds or subtracts known volumes can be used to "calibrate" a specific volume displacement to change in height to determine the volume change in tanks that have irregular shapes or protrusions such as pipes, pumps or other irregular shapes in the tank at the height of the tank.

The placement of at least two sensors to measure fluid in a container that is shifting up-and-down from the back-to-the-front. Multiple instantaneous readings allow instant readings that can be used to calculate more precise volume readings of tanks in vehicles that are moving such as ships, planes, cars trucks. A more precise volume measurement can be determined in a shorter time by including multiple sensors, but four sensors can give four axis weight distribution.

Field Testing

A PDS has been installed in a test site involving an intermediate tank used to transfer fuel into hospital gensets and boiler loop system. The 1000 gal. tank stores fuel for two generators and when needed a back-up boiler loop. Fuel is routinely used in by the gensets and when the replenishment level is met (70% of tank level) fueling from main tank(s) is sent to refill the intermediate tank to 90%. A routine test run on the system includes; manually emptying the intermediate tank and initiating a reset. Upon reset, as the tank control system reboots, detects the low liquid level and initiates a refill to the correct height, 90%. Detecting accurate tank levels both in normal operation and through extensive manual test sequences has shown the PDS to be robust in its function through climate extremes and a robust test protocol.

PDS Operation

The pressure transducer is directly soldered to the printed circuit board and immediately routed through the 24 bit analog to digital processor. The A-to-D processor outputs directly to the 32 bit processor which does all the math and statistics to output the depth and gallonage of the fluid the transducer is testing/monitoring.

The interface box has the external pressure sensor and communicates that to the PDS for real-time pressure compensation.

This information from the PDS is passed to the PDS interface box via RS 485 communication and from the interface box to a computer that has the VMI PDS reporting software. The reporting software may be in a laptop computer such that a tester may move from site to site saving the information, transmitting the information through such communications as the laptop is capable of, or printing the information. The PDS may also be reporting to a standalone computer at a site that is continuously monitoring tanks and reporting Alarms by horn or light, or outputting an alarm to tank monitoring equipment designed to communicate alarms appropriately as the site has specified, or the PDS computer may be connected to communication systems directly. Such direct connection may allow remote monitoring and reporting of alarms as well as all real-time data gathered, including passed test and alarm or reporting level events. Such equipment can be configured to allow modification of programs to accommodate upgrades or "bug" fixes.

One such application is to allow information to be shared with Building Management Systems that monitor important equipment such as tank fuel level, line leak detection, overfill alarms, security systems, oxygen delivery systems, heating and cooling equipment, etc.

Such equipment can be connected with other VMI programs to control pumps, valves, filtration, chemical injectors for bacteria issues, etc.

Global Data Structure variables for calculation of fuel properties include:
Current
Pressure;
Pressure depth
Calculated actual depth
Internal temperature
On chip temperature
State
Input
Calibrated ADC count/mbar
IS Modules State
Pressure ADC Value
Internal Temperature ADC value
On Chip Temperature ADC value The PDS may also have a 24-bit fluid conductivity sensor to allow determination of the water % in the fuel. The barometric sensor has a 24-bit temperature sensor so TCV can also be very accurate.

One may put the same pressure sensor in the external USB sensor to give us current barometric pressure. Minus this value from the absolute and we have actual fluid weight. A 1200 mBar absolute SMT pressure sensor may mount on the PDS PCB. Adding the two values together gives us absolute measure depth.

A 32-bit processor is preferably used and connected to PDS sensor pressure transducer. A 24-bit processor may be connected to the processor to provide ADC. Preferably, these items are contained in the PDS sensor item shown in FIGS. 4-5. The system may communicate to a box via USB, or other, cable. The box may include a standard computer that is protected from the elements. Alternatively, a wireless signal may be emitted for control by a management system further away from the tank. A wire, or wireless, communication system may allow the PDS to communicate with a computer, such as a laptop, that runs software capable of providing output to a user. The computer may also include memory to record and store data. The computer may also be configured to provide reports, alarms, etc.

Figure 5:
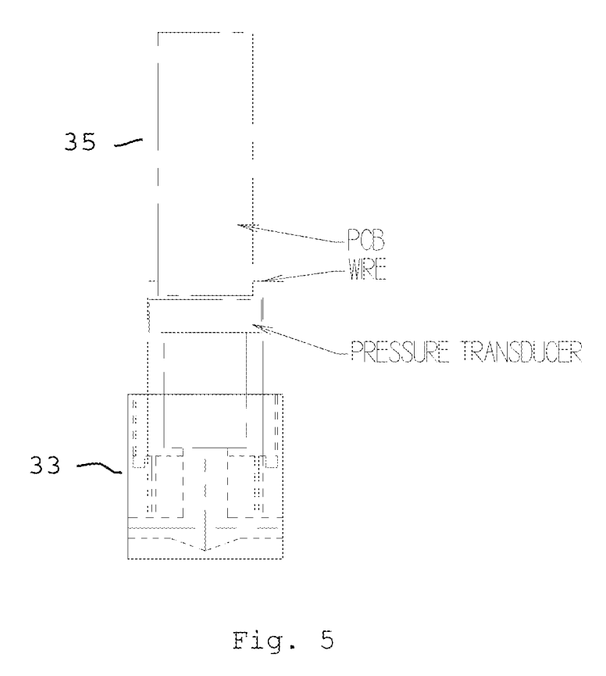
FIG. 5 demonstrates exploded view of PDS sensor.
Figure 5A:
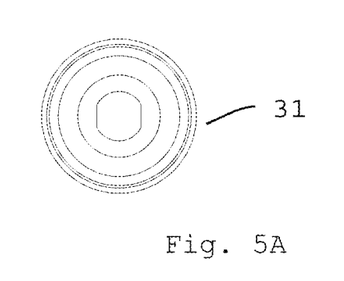
FIG. 5A demonstrates a cross-section of top of PDS sensor.
Figure 5B:
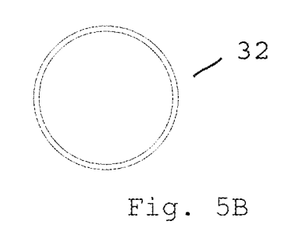
FIG. 5B demonstrates a cross-section of center of PDS sensor.
Figure 5C:
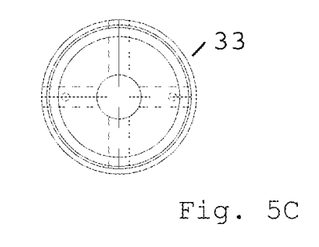
FIG. 5C demonstrates a cross-section of bottom of PDS sensor.

PDS sensor 30 is shown. Center cylinder 32 is preferably hollow to contain circuit board and other onboard components. Top cap 31 may be used to seal PDS, and bottom cap 33 may be similarly used. Transducer may be exposed through PDS sensor surface to allow measurements to be taken. Additionally, wire may communicate information and/or power to components in PDS sensor through shell 32 or top or bottom of PDS. PCB 35 may be included and shielded within PDS.

I claim:

1. A method of determining the qualities of a liquid in a storage tank with an embedded sensor submerged into the liquid, with the embedded sensor at a location at a bottom surface of the storage tank or not more than a few inches above the bottom surface, said method comprising the steps of measuring an initial pressure at a specific location at the bottom of the storage tank to obtain a pressure reading; determining a weight of a fuel based on the initial pressure reading; calibrating a measurement via use of a submersible displacement rod via suspending a rod of a set volume into the fuel; detecting a further pressure; determining a change in the pressure as between the initial pressure and the further pressure readings to determine a pressure differential; setting the pressure differential to determine a pressure to volume ratio; and thereafter monitoring the pressure reading at the embedded sensor.

2. A method as set forth in claim 1 wherein the embedded sensor rests on the bottom of a fuel storage tank.

3. A method as set forth in claim 1 wherein the embedded sensor rests no more than one inch from the bottom of a fuel storage tank.

4. The method as set forth in claim 1 further comprising the step of removing the submersible displacement rod from the fuel.

5. The method as set forth in claim 4 wherein said step of monitoring comprises taking multiple further pressure readings at a set time interval; and comparing the initial, further, and at least one additional pressure readings to determine a weight change of the fuel (based on pressure change reading) to detect a leak.

6. The method of claim 1 whereby said step of measuring is conducted by exposing a pressure transducer in the embedded sensor directly to the fuel pressure.

7. The method of claim 6 whereby said step of detecting is conducted by exposing a pressure transducer in the embedded sensor directly to the fuel pressure.

8. The method of claim 1 whereby said step of determining a change is conducted utilizing a TCV formula to determine if differences of fluid level over time are due to natural ambient conditions, or system failure.

9. The method of claim 8 whereby the embedded sensor at the bottom surface of the storage tank is at a known height within the fuel.

10. The method for determining the qualities of a liquid in a storage tank as set forth in claim 1, further comprising the step of measuring an ambient condition via a secondary sensor.

11. A method such as in claim 10 whereby the embedded sensor determines at least a first property of a stored liquid, and compares the at least first property with an expected change of system conditions simultaneously reported by the secondary sensor.

12. A method such as in claim 1 whereby the embedded sensor determines a conductivity or a resistance of the liquid.

13. The method as set forth in claim 12 wherein the embedded sensor compares conductivity or resistance with an expected change of system conditions reported by a secondary sensor detecting ambient conditions.

14. The method such as in claim 12 whereby the conductivity or resistance of the liquid determines a water percentage in the fuel.

* * * * *

UNITED STATES PATENT AND TRADEMARK OFFICE
CERTIFICATE OF CORRECTION

| | |
|---|---|
| PATENT NO. | : 11,274,635 B2 |
| APPLICATION NO. | : 16/666183 |
| DATED | : March 15, 2022 |
| INVENTOR(S) | : Gregory E. Young |

It is certified that error appears in the above-identified patent and that said Letters Patent is hereby corrected as shown below:

In the Claims

In Column 16, Line 12, Claim 9, delete the word "surface".

Signed and Sealed this
Thirtieth Day of August, 2022

Katherine Kelly Vidal
*Director of the United States Patent and Trademark Office*